United States Patent
Wachtler et al.

[11] Patent Number: 5,250,220
[45] Date of Patent: Oct. 5, 1993

[54] 2,5-DISUBSTITUTED HETEROCYCLIC COMPOUNDS, AND A LIQUID-CRYSTALLINE MEDIUM

[75] Inventors: Andreas Wachtler, Griesheim; Reinhard Hittich, Modautal; Eike Poetsch, Mühltal; Joachim Krause, Dieburg; Ulrich Finkenzeller, Plankstadt, all of Fed. Rep. of Germany; David Coates, Merley, Great Britain

[73] Assignee: Merck Patent Gesellschaft Mit Beschränkter Haftung, Darmstadt, Fed. Rep. of Germany

[21] Appl. No.: 947,085

[22] Filed: Sep. 18, 1992

Related U.S. Application Data

[63] Continuation of Ser. No. 585,126, filed as PCT/EP90/01318, Aug. 10, 1990, published as WO91/02780, Mar. 7, 1991, abandoned.

[30] Foreign Application Priority Data

Aug. 12, 1989 [DE] Fed. Rep. of Germany ....... 3926745
Sep. 5, 1989 [DE] Fed. Rep. of Germany ....... 3929421

[51] Int. Cl.$^5$ .................... C09K 19/34; C09K 19/30; C07D 319/06
[52] U.S. Cl. .................. 252/299.61; 252/299.01; 252/299.63; 549/369; 549/374
[58] Field of Search .............. 252/299.01, 299.61, 252/299.63; 544/242, 298; 359/103, 104; 549/369, 374

[56] References Cited

U.S. PATENT DOCUMENTS

| | | | |
|---|---|---|---|
| 4,180,475 | 12/1979 | Schadt et al. | 252/299 |
| 4,309,539 | 1/1982 | Boller et al. | 544/242 |
| 4,581,155 | 4/1986 | Goto et al. | 252/299.61 |
| 4,776,975 | 10/1988 | Sawada et al. | 252/299.63 |
| 4,784,471 | 11/1988 | Wächtler et al. | 350/350 R |
| 5,021,189 | 6/1991 | Sawada et al. | 252/299.61 |
| 5,122,295 | 6/1992 | Weber et al. | 252/299.01 |
| 5,171,472 | 12/1992 | Tanaka et al. | 252/299.61 |

FOREIGN PATENT DOCUMENTS

| | | |
|---|---|---|
| 0315014 | 5/1989 | European Pat. Off. |
| 3732284 | 4/1989 | Fed. Rep. of Germany |
| 3909802 | 4/1990 | Fed. Rep. of Germany |
| 2216523 | 10/1989 | United Kingdom |

*Primary Examiner*—Robert L. Stoll
*Assistant Examiner*—Shean C. Wu
*Attorney, Agent, or Firm*—Millen, White, Zelano & Branigan

[57] ABSTRACT

Novel 2,5-disubstituted heterocyclic compounds of the formula I

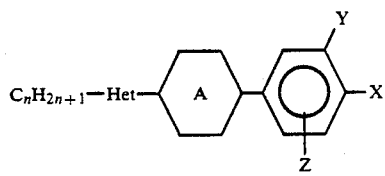

in which
n is 1 to 10,
Het is

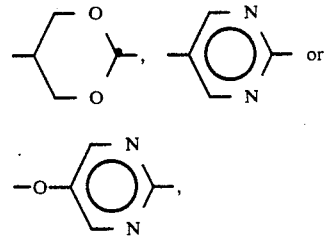

Ring A is trans-1,4-cyclohexylene or, in the case where Het =

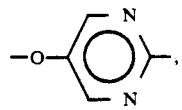

X = —OCF$_3$ or —OCHF$_2$ and/or Y = Z = F, is alternatively 1,4-phenylene,
X is CN, F, Cl, —CF$_3$, —OCF$_3$ or —OCHF$_2$, and
Y and Z are each, independently of one another, H or F, can be used as components of liquid-crystalline media.

9 Claims, No Drawings

2,5-DISUBSTITUTED HETEROCYCLIC COMPOUNDS, AND A LIQUID-CRYSTALLINE MEDIUM

This application is a continuation of application Ser. No. 07/585,126, filed as PCT/EP90/01318, Aug. 10, 1990, published as WO91/02780, Mar. 7, 1991, now abandoned.

The invention relates to novel 2,5-disubstituted heterocyclic compounds of the formula I

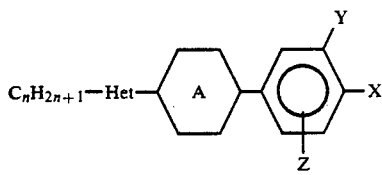

wherein
n is 1 to 10,
Het is

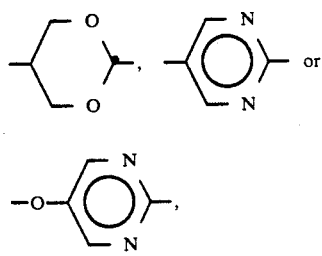

Ring A is trans-1,4-cyclohexylene or, in the case where Het=

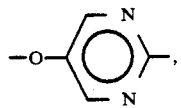

$X =$ —$OCF_3$ or —$OCHF_2$ and/or $Y = Z = F$, is alternatively 1,4-phenylene,

X is CN, F, Cl, —$CF_3$, —$OCF_3$ or —$OCHF_2$, and Y and Z are each, independently of one another, H or F.

German Offenlegungsschrift 32 07 114 discloses similar compounds of the formula

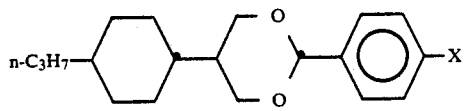

in which X is F, Cl, Br, $CF_3$ or CN. However, these compounds do not satisfy extreme requirements regarding chemical stability, as demanded, for example, for displays having an active matrix.

EP-A 0 193 191 discloses similar compounds of the formula

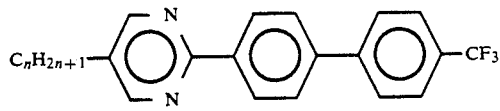

in which n is 2 to 6. However, these compounds have melting points significantly above 125° C. and have exclusively smectic phases.

Like similar compounds disclosed, for example, in German Offenlegungsschriften 29 44 905 and 27 02 591, the compounds of the formula I can be used as components of liquid-crystalline media, in particular for displays based on the principle of the twisted cell.

All the substances employed hitherto for this purpose have certain disadvantages, for example excessively high melting points, excessively low clear points, excessively low stability to the action of heat, light or electrical fields, excessively low electrical resistance, and an excessive temperature dependency of the threshold voltage.

The materials employed hitherto have disadvantages, in particular in the case of displays of the supertwist type (STN) having twist angles of significantly greater than 220° C. [sic] or in the case of displays having an active matrix.

The invention had the object of finding novel liquid-crystalline compounds which are suitable as compounds of liquid-crystalline media, in particular for nematic media having a positive dielectric anisotropy, and which do not have the disadvantages of the known compounds, or only do so to a reduced extent. This object has been achieved by the provision of the novel compounds of the formula I.

It has been found that the compounds of the formula I are preeminently suitable as components of liquid-crystalline media. In particular, they can be used to obtain liquid-crystalline media having broad nematic ranges, excellent nematogeneity down to low temperatures, excellent chemical stability, a pronounced $\epsilon$ with a positive dielectric anisotropy, low temperature dependency of the threshold voltage and/or low optical anisotropy. In addition, the novel compounds have good solubility for other components of media of this type and a high positive dielectric anisotropy at the same time as favorable viscosity.

The compounds of the formula I make it possible to produce both STN displays having a very steep electro-optical characteristic line and displays having an active matrix with excellent long-term stability.

In the pure state, the compounds of the formula I are colorless and form liquid-crystalline mesophases in a temperature range in a favorable location for electro-optical use.

The invention thus relates to the compounds of the formula I and to the use of the compounds of the formula I as components of liquid-crystalline media, liquid-crystalline media containing at least one compound of the formula I, and electrooptical displays which contain media of this type.

Above and below, n, A, X, Y and Z are as defined above, unless expressly stated otherwise.

In the compounds of the formula I, the alkyl groups $C_nH_{2n+1}$ are preferably straight-chain. Accordingly, $C_nH_{2n+1}$ is preferably methyl, ethyl, n-propyl, n-butyl, n-pentyl, n-hexyl, n-heptyl, n-octyl, n-nonyl or n-decyl. n is preferably 2, 3, 4 or 5.

Compounds of the formula I containing branched alkyl groups may occasionally be of importance due to better solubility in the customary liquid-crystalline base materials, but in particular as chiral dopes if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-heptyl (=1-methylhexyl), 2-octyl (=1-methylheptyl) and 2-ethylhexyl.

The radical

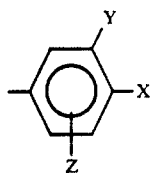

is preferably

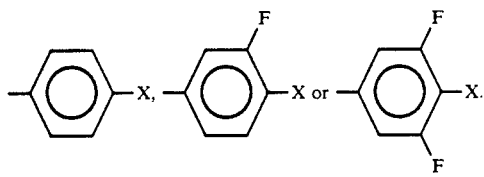

X is preferably F, Cl, —CF$_3$, —OCHF$_2$ or —OCF$_3$.

Particular preference is given to the 2-(trans-4-phenylcyclohexyl)-5-alkyl-1,3-dioxanes of the formula Ia

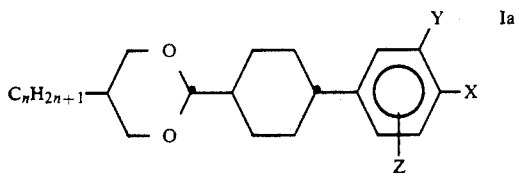

in which n is 1 to 10, X is F, Cl, —CF$_3$, —OCF$_3$ or —OCHF$_2$, and Y and Z are each, independently of one another, H or F, and the 2,5-disubstituted pyrimidines of the formula Ib

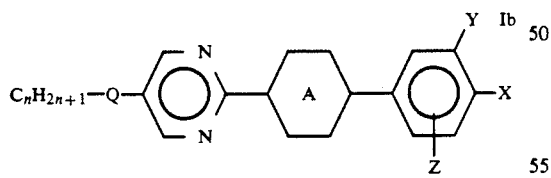

in which n is 1 to 10, Q is —O— or a single bond, A is trans-1,4-cyclohexylene or 1,4-phenylene, X is F, Cl, —CF$_3$, —OCF$_3$ or —OCHF$_2$, and Y and Z are each, independently of one another, H or F.

Q is preferably a single bond.

In addition, the compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the reactions mentioned. Use can also be made here of variants which are known per se, but are not described in greater detail.

If desired, the starting materials can also be formed in situ by not isolating oneself [sic] from the reaction mixture, but instead reacting oneself [sic] further to form the compounds of the formula I.

The 1,3-dioxanes are preferably prepared by reacting an aldehyde of the formula II

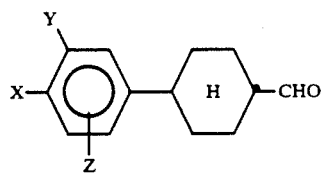

in which X, Y and Z are as defined above, or a functional derivative thereof, with a diol of the formula III $$(HOCH_2)_2—CH—C_nH_{2n+1}$$ III in which n is as defined above.

The compounds of the fomulae II and III are expediently reacted with one another in the presence of an inert solvent, such as benzene or toluene, and/or in the presence of a catalyst, for example a strong acid, such as sulfuric acid, benzenesulfonic acid or p-toluenesulfonic acid, at temperatures between about 20 and about 150, preferably between 80° and 120°. Suitable reactive derivatives of the compounds of the formulae II and III are primarily simple acetals.

Some of the starting materials of the formulae II and III and the reactive derivatives thereof are known, and some can be prepared without difficulty from compounds known from the literature by standard methods of organic chemistry. For example, the aldehydes of the formula II can be obtained by oxidation of corresponding alcohols or by reduction of corresponding carboxylic acids (or derivatives thereof), and the diols of the formula III can be obtained by reduction of corresponding diesters of the formula (alkylOOCCH$_2$)$_2$—CH—C$_n$H$_{2n+1}$.

The precursors which are suitable for the synthesis of the aldehydes of the formula II can be obtained, for example, by the following synthetic scheme:

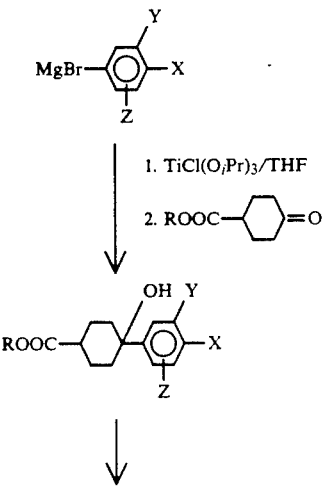

5
-continued

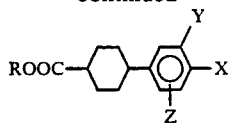

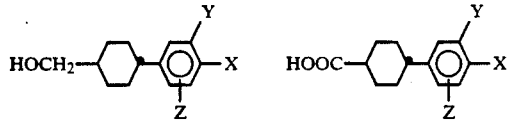

The Grignard compound obtained from the corresponding bromobenzene derivative is reacted with chlorotrialkyl orthotitanate or -zirconate by the method of WO 87/05599 to give the tertiary cyclohexanol. After elimination of water, hydrogenation of the double bond and isomerization, the trans-cyclohexanecarboxylate is obtained by conventional methods. From the latter, the suitable precursors for the aldehydes of the formula II are obtained by conventional standard methods.

The pyrimidines are preferably prepared by condensing corresponding amidines in accordance with route 2 to give the compounds according to the invention. The amidines can be prepared as shown in scheme 1.

Scheme 1

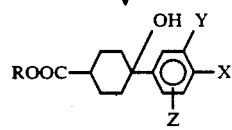

6
-continued
Scheme 1

1. TiCl(O$_i$Pr)$_3$/THF
2. ROOC—⬡=O

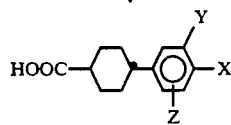    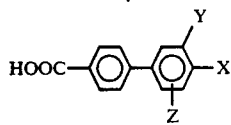

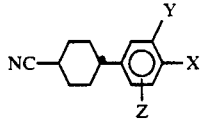    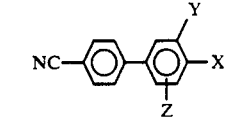

1. Toluene/    HCl      1. Toluene/    HCl
   MeOH                  MeOH
2. NH$_3$                   2. NH$_3$

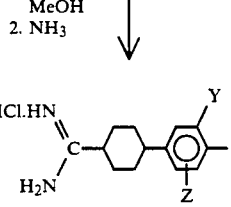    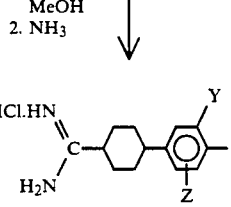

Scheme 2

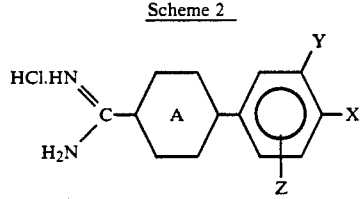

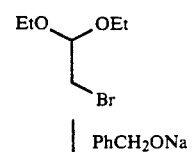

PhCH$_2$ONa

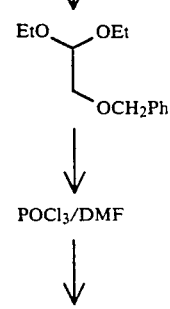

POCl$_3$/DMF

-continued
Scheme 2

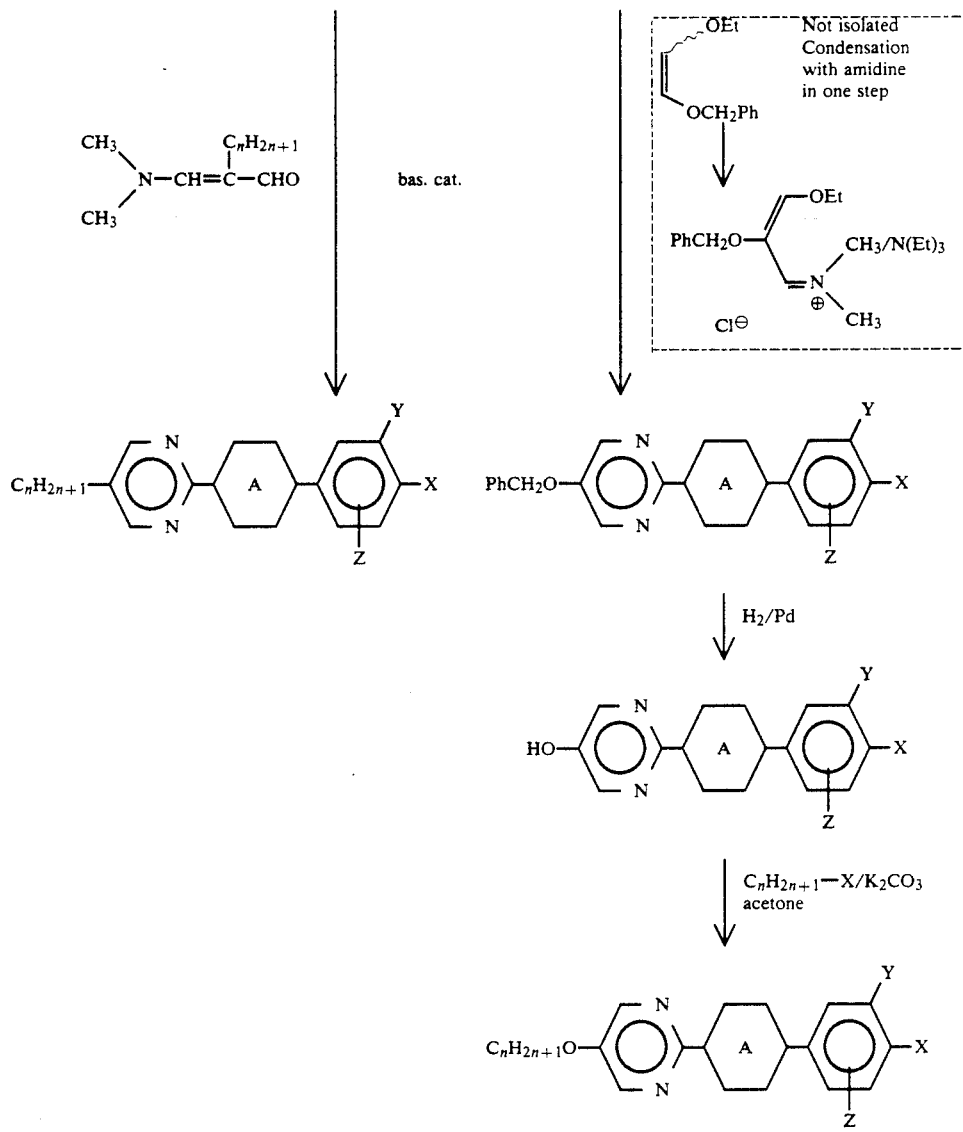

The Grignard compound obtained from the corresponding bromobenzene derivative is reacted with chlorotrialkyl orthotitanate or -zirconate by the method of WO 87/05599 to give the tertiary cyclohexanol. After elimination of water, hydrogenation of the double bond and isomerization or dehydrogenation, the trans-cyclohexanecarboxylic acid or benzoic acid is obtained by conventional methods. From the latter, the suitable precursors for the amidines are obtained by conventional standard methods.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylicacid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

R'—L—E—R''                    1

R'—L—COO—E—R''                2

R'—L—OOC—E—R''                3

R'—L—CH$_2$CH$_2$—E—R''       4

R'—L—C≡C—E—R''                5

In the formulae 1, 2, 3, 4 and 5, L and E, which may be identical or different, are in each case, independently of one another, a bivalent radical from the group formed by —Phe—, —Cyc—, —Phe—Phe, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R'' are in each case, independently of one another, alkyl, alkenyl, alkoxy, alkenyloxy or alkanoyloxy having up to 8 carbon atoms. In most of these compounds, R' and R'' are different from one another, one of these radicals usually being alkyl or alkenyl. In the compounds of the sub-formulae 1b, 2b, 3b, 4b and 5b, R'' is —CN, —CF$_3$, —OCF$_3$, F, Cl or —NCS; in this case, R has the meaning given for the compounds of the sub-formulae 1a to 5a and is preferably alkyl or alkenyl. R'' is preferably selected from the group comprising —F, Cl, CF$_3$ and —OCF$_3$. However, other variants of the proposed substituents in the compounds of the formulae 1, 2, 3, 4 and 5 are common.

Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

| DAST | Diethylaminosulfur trifluoride |
|---|---|
| DCC | Dicyclohexylcarbodiimide |
| DDQ | Dichlorodicyanobenzoquinone |
| DIBALH | Diisobutylaluminum hydride |
| DMSO | Dimethyl sulfoxide |
| POT | Potassium tertiary-butanolate |
| THF | Tetrahydrofuran |
| pTSOH | p-Toluenesulfonic acid |

EXAMPLE 1

A mixture of 2.2 g of trans-4-(3,4-difluorophenyl)-cyclohexanecarbaldehyde (obtainable by converting the corresponding acid into the chloride and Rosenmund reduction), 1.32 g of 2-butylpropane-1,3-diol, 0.01 g of p-toluenesulfonic acid and 15 ml of toluene is boiled on a water separator for 3 hours, cooled, washed with water and evaporated, to give 2-[trans-4-(3,4-difluorophenyl)cyclohexyl]-5-butyl-1,3-dioxane.

EXAMPLES 2 TO 41

The following compounds are obtained analogously to Example 1 from the corresponding aldehydes and the corresponding 1,3-diols:

|  | n | X | Y | Z |
|---|---|---|---|---|
| (2) | 2 | F | F | H |

-continued

| | n | X | Y | Z |
|---|---|---|---|---|
| (3) | 3 | F | F | H |
| (4) | 5 | F | F | H |
| (5) | 7 | F | F | H |
| (6) | 2 | F | H | H |
| (7) | 3 | F | H | H |
| (8) | 4 | F | H | H |
| (9) | 5 | F | H | H |
| (10) | 2 | Cl | H | H |
| (11) | 3 | Cl | H | H |
| (12) | 4 | Cl | H | H |
| (13) | 5 | Cl | H | H |
| (14) | 2 | Cl | F | H |
| (15) | 3 | Cl | F | H |
| (16) | 4 | Cl | F | H |
| (17) | 5 | Cl | F | H |
| (18) | 2 | $CF_3$ | H | H |
| (19) | 3 | $CF_3$ | H | H |
| (20) | 4 | $CF_3$ | H | H |
| (21) | 5 | $CF_3$ | H | H |
| (22) | 2 | $OCF_3$ | H | H |
| (23) | 3 | $OCF_3$ | H | H |
| (24) | 4 | $OCF_3$ | H | H |
| (25) | 5 | $OCF_3$ | H | H |
| (26) | 2 | $OCHF_2$ | H | H |
| (27) | 3 | $OCHF_2$ | H | H |
| (28) | 4 | $OCHF_2$ | H | H |
| (29) | 5 | $OCHF_2$ | H | H |
| (30) | 2 | CN | H | H |
| (31) | 3 | CN | H | H |
| (32) | 4 | CN | H | H |
| (33) | 5 | CN | H | H |
| (34) | 2 | CN | F | H |
| (35) | 3 | CN | F | H |
| (36) | 4 | CN | F | H |
| (37) | 5 | CN | F | H |
| (38) | 2 | CN | F | F* |
| (39) | 3 | CN | F | F* |
| (40) | 4 | CN | F | F* |
| (41) | 5 | CN | F | F* |

*Z in the ortho-position to X

EXAMPLE 42

0.01 mol of 4-(3,4-difluorophenyl)benzamidine hydrochloride and 0.01 mol of α-propyl-β-dimethylaminoacrolein are introduced into a solution of sodium methylate and methanol, and the mixture is refluxed for 5 hours. The methanol is evaporated off, the residue is taken up in toluene, and the solution is subjected to customary aqueous work-up, to give 5-n-propyl-2-[4-(3,4-difluorophenyl)phenyl]pyrimidine.

EXAMPLES 143 TO 122

The following compounds are obtained analogously to Example 42 from the corresponding amines:

| | n | X | Y | Z | Q | A |
|---|---|---|---|---|---|---|
| (43) | 2 | F | F | H | — | —Phe— |
| (44) | 4 | F | F | H | — | —Phe— |
| (45) | 5 | F | F | H | — | —Phe— |
| (46) | 7 | F | F | H | — | —Phe— |
| (47) | 2 | F | H | H | — | —Phe— |
| (48) | 3 | F | H | H | — | —Phe— |
| (49) | 4 | F | H | H | — | —Phe— |
| (50) | 5 | F | H | H | — | —Phe— |
| (51) | 2 | Cl | H | H | — | —Phe— |
| (52) | 3 | Cl | H | H | — | —Phe— |
| (53) | 4 | Cl | H | H | — | —Phe— |
| (54) | 5 | Cl | H | H | — | —Phe— |
| (55) | 2 | Cl | F | H | — | —Phe— |
| (56) | 3 | Cl | F | H | — | —Phe— |
| (57) | 4 | Cl | F | H | — | —Phe— |
| (58) | 5 | Cl | F | H | — | —Phe— |
| (59) | 2 | $CF_3$ | H | H | — | —Phe— |
| (60) | 3 | $CF_3$ | H | H | — | —Phe— |
| (61) | 4 | $CF_3$ | H | H | — | —Phe— |
| (62) | 5 | $CF_3$ | H | H | — | —Phe— |
| (63) | 2 | $OCF_3$ | H | H | — | —Phe— |
| (64) | 3 | $OCF_3$ | H | H | — | —Phe— |
| (65) | 4 | $OCF_3$ | H | H | — | —Phe— |
| (66) | 5 | $OCF_3$ | H | H | — | —Phe— |
| (67) | 2 | $OCHF_2$ | H | H | — | —Phe— |
| (68) | 3 | $OCHF_2$ | H | H | — | —Phe— |
| (69) | 4 | $OCHF_2$ | H | H | — | —Phe— |
| (70) | 5 | $OCHF_2$ | H | H | — | —Phe— |
| (71) | 2 | CN | H | H | — | —Phe— |
| (72) | 3 | CN | H | H | — | —Phe— |
| (73) | 4 | CN | H | H | — | —Phe— |
| (74) | 5 | CN | H | H | — | —Phe— |
| (75) | 2 | CN | F | H | — | —Phe— |
| (76) | 3 | CN | F | H | — | —Phe— |
| (77) | 4 | CN | F | H | — | —Phe— |
| (78) | 5 | CN | F | H | — | —Phe— |
| (79) | 2 | CN | F | F* | — | —Phe— |
| (80) | 3 | CN | F | F* | — | —Phe— |
| (81) | 4 | CN | F | F* | — | —Phe— |
| (82) | 5 | CN | F | F* | — | —Phe— |
| (83) | 2 | F | F | H | — | —Cyc— |
| (84) | 4 | F | F | H | — | —Cyc— |
| (85) | 5 | F | F | H | — | —Cyc— |
| (86) | 7 | F | F | H | — | —Cyc— |
| (87) | 2 | F | H | H | — | —Cyc— |
| (88) | 3 | F | H | H | — | —Cyc— |
| (89) | 4 | F | H | H | — | —Cyc— |
| (90) | 5 | F | H | H | — | —Cyc— |
| (91) | 2 | Cl | H | H | — | —Cyc— |
| (92) | 3 | Cl | H | H | — | —Cyc— |
| (93) | 4 | Cl | H | H | — | —Cyc— |
| (94) | 5 | Cl | H | H | — | —Cyc— |
| (95) | 2 | Cl | F | H | — | —Cyc— |
| (96) | 3 | Cl | F | H | — | —Cyc— |
| (97) | 4 | Cl | F | H | — | —Cyc— |
| (98) | 5 | Cl | F | H | — | —Cyc— |
| (99) | 2 | $CF_3$ | H | H | — | —Cyc— |
| (100) | 3 | $CF_3$ | H | H | — | —Cyc— |
| (101) | 4 | $CF_3$ | H | H | — | —Cyc— |
| (102) | 5 | $CF_3$ | H | H | — | —Cyc— |
| (103) | 2 | $OCF_3$ | H | H | — | —Cyc— |
| (104) | 3 | $OCF_3$ | H | H | — | —Cyc— |
| (105) | 4 | $OCF_3$ | H | H | — | —Cyc— |
| (106) | 5 | $OCF_3$ | H | H | — | —Cyc— |
| (107) | 2 | $OCHF_2$ | H | H | — | —Cyc— |
| (108) | 3 | $OCHF_2$ | H | H | — | —Cyc— |
| (109) | 4 | $OCHF_2$ | H | H | — | —Cyc— |
| (110) | 5 | $OCHF_2$ | H | H | — | —Cyc— |
| (111) | 2 | CN | H | H | — | —Cyc— |
| (112) | 3 | CN | H | H | — | —Cyc— |
| (113) | 4 | CN | H | H | — | —Cyc— |
| (114) | 5 | CN | H | H | — | —Cyc— |
| (115) | 2 | CN | F | H | — | —Cyc— |
| (116) | 3 | CN | F | H | — | —Cyc— |
| (117) | 4 | CN | F | H | — | —Cyc— |
| (118) | 5 | CN | F | H | — | —Cyc— |
| (119) | 2 | CN | F | F* | — | —Cyc— |
| (120) | 3 | CN | F | F* | — | —Cyc— |
| (121) | 4 | CN | F | F* | — | —Cyc— |
| (122) | 5 | CN | F | F* | — | —Cyc— |

*Z in the ortho-position is X

The following are examples of media containing at least one compound of the formula I:

EXAMPLE A

A mixture comprising

7% of p-(trans-4-propylcyclohexyl)benzonitrile,
5% of p-(trans-4-butylcyclohexyl)benzonitrile,
24% of p-(trans-4-pentylcyclohexyl)fluorobenzene,
14% of p-(trans-4-heptylcyclohexyl)fluorobenzene,
15% of 2-[trans-4-(3,4-difluorophenyl)cyclohexyl]-5-butyl-1,3-dioxane,
18 % of 2-[trans-4-(p-fluorophenyl)cyclohexyl]-5-butyl-1,3-dioxanes [sic] and 17% of 2-[trans-4-(p-fluorophenyl)cyclohexyl]-5-butyl-1,3-dioxane
has a high electrical resistance.

We claim:

1. A 2,5-disubstituted heterocyclic compound of the formula

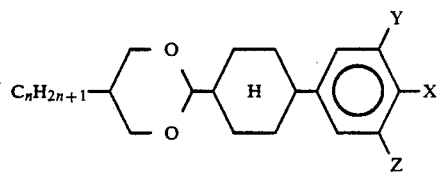

in which
n is 1 to 10,
X is —CF$_3$, —OCF$_3$ or —OCHF$_2$, and
Y and Z are each, independently of one another, H or F.

2. A compound according to claim 1, wherein X=CF$_3$, Y=F, and Z=H or F.

3. A compound according to claim 1, wherein X=OCF$_3$, Y=F, and Z=H or F.

4. A compound according to claim 1, wherein X=OCF$_3$, Y=H and Z=H.

5. Heterocyclic compounds according to claim 1, characterized in that X is —CF$_3$ or —OCF$_3$.

6. Heterocyclic compounds according to claim 1, characterized in that Y=Z=H.

7. Heterocyclic compounds according to claim 1, characterized in that Y=F and Z=H or F.

8. A liquid-crystalline medium for electrooptical comprising at least two liquid-crystalline components, wherein at least one component is a heterocyclic compound according to claim 1.

9. An electrooptical display comprising a liquid-crystal cell, wherein the liquid-crystal cell contains a medium according to claim 8.

* * * * *